US005693837A

United States Patent [19]

Smith et al.

[11] Patent Number: 5,693,837

[45] Date of Patent: Dec. 2, 1997

[54] FERRIC ALKYL AMINE CITRATES AND METHODS OF MAKING THEM

[75] Inventors: Kevin W. Smith, McMurray; Leonard J. Persinski, Pittsburgh, both of Pa.

[73] Assignee: Clearwater, Inc., Pittsburgh, Pa.

[21] Appl. No.: 684,099

[22] Filed: Jul. 22, 1996

Related U.S. Application Data

[60] Division of Ser. No. 580,171, Dec. 28, 1995, Pat. No. 5,571,315, which is a continuation-in-part of Ser. No. 360, 438, Dec. 21, 1994, abandoned, which is a division of Ser. No. 209,266, Mar. 14, 1994, Pat. No. 5,417,287.

[51] Int. Cl.[6] .............................. C09K 7/06; C09K 7/00; C09K 15/02

[52] U.S. Cl. .......................... 556/148; 507/238; 507/260; 507/922; 507/921; 106/285; 106/287.18; 556/146

[58] Field of Search .................................... 507/238, 260, 507/921, 922; 556/146, 148; 106/285, 287.18

[56] References Cited

U.S. PATENT DOCUMENTS

| | | | |
|---|---|---|---|
| 2,644,828 | 7/1953 | Kruse et al. | 260/439 |
| 3,348,613 | 10/1967 | Irani et al. | 166/307 |
| 3,496,222 | 2/1970 | Quimby et al. | 560/231 |
| 3,504,004 | 3/1970 | Roos | 556/148 |
| 4,003,393 | 1/1977 | Jaggard et al. | 137/15 |
| 4,153,649 | 5/1979 | Griffin, Jr. | 558/110 |
| 4,174,283 | 11/1979 | Griffin, Jr. | 216/786 |
| 4,200,540 | 4/1980 | Burnham | 507/238 |
| 4,316,810 | 2/1982 | Burnham | 507/238 |
| 4,476,930 | 10/1984 | Watanabe | 166/279 |
| 4,605,068 | 8/1986 | Young et al. | 166/307 |
| 4,622,155 | 11/1986 | Harris et al. | 507/238 |
| 5,417,287 | 5/1995 | Smith et al. | 166/308 |
| 5,571,315 | 11/1996 | Smith et al. | 106/285 |
| 5,647,900 | 7/1997 | Smith et al. | 106/285 |

*Primary Examiner*—Sharon Gibson
*Assistant Examiner*—Valerie Fee
*Attorney, Agent, or Firm*—William L. Krayer

[57] ABSTRACT

This invention relates to improved hydrocarbon gels which find use in the fracturing of petroleum producing formations. In particular it relates to the use of a defined class of gelling agents for hydrocarbons which provide excellent results in such fracturing. The gelling agents comprise combinations of selected orthophosphate esters and ferric ammonium citrate or lower alkyl amine derivative thereof. The lower alkyl amine derivatives are referred to as ferric alkylamine citrates.

8 Claims, No Drawings

FERRIC ALKYL AMINE CITRATES AND METHODS OF MAKING THEM

RELATED APPLICATIONS

This application is a division of U.S. patent application Ser. No. 08/580.171, filed Dec. 28, 1995, now U.S. Pat. No. 5,571,315 which is a continuation-in-part of U.S. patent application 08/360,438 filed Dec. 21, 1994 abandoned, which is a division of application Ser. No. 08/209,266 filed Mar. 14, 1994, now U.S. Pat. No. 5,417,287.

TECHNICAL FIELD

This invention relates to improved hydrocarbon gels which find use in petroleum producing formation fracturing. In particular it relates to the use of a defined class of gelling agents for hydrocarbons which provide excellent results in such fracturing. The gelling agents are combinations of selected orthophosphate esters and ferric ammonium citrate and/or lower alkyl derivatives thereof.

BACKGROUND OF THE INVENTION

The development of the use of gelled hydrocarbons as fracturing fluids is reviewed by Weldon M. Harms in a chapter entitled "Application of Chemistry in Oil and Gas Well Fracturing", at pages 59–60 of the book "Oil-Field Chemistry (ACS Symposium #396—1988)" published by the American Chemical Society in 1989. The basic technique of formation fracturing involves the injection of a fracturing fluid down the well bore, which is usually cemented in place and at least 0.3 mile long, and then through horizontal holes in the steel pipe, or casing, of the well, to obtain access to the subterranean formation. The fracturing fluid is under high pressure and must be able to survive the severe shear forces caused when flow is forced through the casing perforations of perhaps ¼ to ½ inch in diameter, as well as the shear forces encountered at the leading edge of the fracture. Whatever chemical additives are used to influence viscosity, induce gel formation, stabilize against resident chemicals, pH or temperature conditions in the formation, inhibit scale formation or corrosion, or inhibit paraffin deposition, for example, must also be able to withstand the shear forces and other inhospitable conditions of use. Most commonly available liquids typically are viscosified before they are particularly effective in carrying the large quantities of proppants widely used in the fracturing process.

When hydrocarbons are used in the fracturing process, they are commonly treated to increase their viscosity. As reviewed by Harms, an early viscosifying agent was napalm, an aluminum soap of fatty acids. Aluminum salts of orthophosphate esters were introduced in the late 1960's, followed by the suggestion of the use of $Fe_3O_4$ for combination with the orthophosphate esters, in Monroe U.S. Pat. No. 3,505,374. While many other combinations of metals, and other materials have been suggested as viscosifying agents, aluminum crosslinked orthophosphate esters are still, according to Harms, the most widely used.

The aluminum compounds present problems, however, particularly where any significant amount of water is present. They generally will not satisfactorily perform the desired crosslinking function in the presence of more than about 1200 ppm of water, nor where the pH is outside a relatively narrow range. Moreover, an inadvertent excess of aluminum compound treatment is detrimental to the desired performance because the aluminum compound itself adversely affects the pH. The iron provided by ferric salts as in the present invention and described in the parent application hereof and in U.S. Pat. No. 5,417,287 (the grandparent of the present application), on the contrary, permits operation in wider pH ranges.

In describing a gel which can be used as a pig in a pipeline, Jaggard et al in U.S. Pat. No. 4,003,393 recite the possibility of iron as one of a number of metals to combine with a class of aliphatic substituted orthophosphoric esters. No other qualifiers are used to describe the iron, however.

In U.S. Pat. No. 4,153,649, Griffin proposes reacting a pentavalent phosphorous compound with a class of hydroxy ethers before employing the metal salt. Among the metal salts he uses is ferric nitrate, but he further requires a "separate source of base" to be used with the hydroxy ether modified phosphates, as spelled out in column 4, lines 55–58 and column 11, lines 37–68. In the latter passage, the ferric nitrate is combined with ethylene diamine tetraacetic acid, a well-known chelating agent.

Monroe, in U.S. Pat. No. 3,505,374, uses a gelling agent for hydrocarbons characterized as a ferroso-ferric salt of an alkyl oleyl diester of orthophosphoric mono acid. The iron compound is further described as magnetite, or $Fe_3O_4$. He suggests this combination for fracturing subterranean oil-bearing formations, but says none of the "other oxidized forms of iron including ferrous and ferric oxides and hydroxides, chlorides, sulfates and nitrates"(col 3, lines 2–4) yielded a gel as obtained with the magnetite.

Burnham, in U.S. Pat. No. 4,200,540, describes a large class of phosphates and phosphate esters which he mixes with aluminum salts, aluminates and aluminum metal. He chooses combinations of the materials as a function of various down-hole temperatures. No mention is made of iron salts; the reference is cited mainly for its comprehensive description of the phosphates deemed to be useful. See also Burnham's U.S. Pat. No. 4,316,810.

A reaction product of citric acid and monoethanolamine is used with phosphoric acid in treating sandstone formations by Young et al in U.S. Pat. No. 4,605,068. The treatment has nothing to do with gelling hydrocarbons, however.

SUMMARY OF THE INVENTION

We have found that ferric salts can be very advantageously used in the gelling of hydrocarbons, particularly for use in formation fracturing, rather than aluminum compounds, for combination with orthophosphate esters. The present continuation-in-part application is concerned specifically with ferric ammonium citrate and/or lower alkyl derivatives thereof such as ferric butyl amine citrate and ferric isopropylamine citrate.

The ferric salts have the advantage that they can be used in the presence of large amounts of water, such as up to 20%. One of the advantages of fracturing with hydrocarbon gels is that some formations may tend to imbibe large quantities of water, while others are water-sensitive and will swell inordinately if water is introduced; our invention permits one to use a hydrocarbon gel in areas where water may cause trouble not only with the formation itself, but with the fracturing agent or the gelling agent. Also, ferric salts are not adversely affected by commonly used alcohols, such as methanol and isopropanol. In addition, they can be used in broad ranges of pH, yet the linkages formed can still be broken with gel breaking additives conventionally used for that purpose. In addition, ferric salts such as ferric sulfate crosslink rapidly and can be made to link even more rapidly with the use of surfactants and/or alkaline or caustic agents such as potassium hydroxide, triethylamine, and triethanolamine.

When dissolved in a hydrocarbon such as gasoline, diesel oil, crude oil, or kerosene, the ferric salt in combination with orthophosphate esters as defined below will cause the hydrocarbon to gel. The gel is generally stable to heat, and the degree of gelling can be controlled by the concentration of orthophosphate ester in the fluid. As further described herein, ferric ammonium citrate and its lower alkyl derivatives generate gels of enhanced strength and temperature resistance. In addition, the apparent chelation of the iron by the citrate moiety inhibits the precipitation of the iron in the form of ferric hydroxide.

DETAILED DESCRIPTION OF THE INVENTION

The phosphate ester which we use is advantageously added first and mixed with the Diesel fuel or other hydrocarbon to be used as the fracturing agent, generally in amounts from about 0.3% to about 1.5% by weight, based on the total. Then the ferric salt, specifically the ferric ammonium citrate or lower alkyl derivative, is added in amounts to provide preferably in the range of about 0.25 mole of ferric iron for each mole of phosphate or phosphate ester to about 2 moles of ferric iron for each mole of phosphate or phosphate ester. In this manner, the process materials can be prepared more or less continuously, as opposed to the batch approach sometimes used in the past. More broadly we may use any amount of ferric salt such as ferric ammonium citrate or a lower alkyl derivative thereof which is effective to make a gel with the phosphate ester. This will be accomplished at about 0.1 to about 2.5 mole of ferric iron for each mole of phosphate ester, preferably 0.8:1 to 1.2:1. Very small amounts (for example less than 0.1 mole/mole of phosphate ester) of ferric ammonium citrate or its lower alkyl derivatives will have at least some gelling effect; amounts over 2 or 2.5 moles/mole of phosphate will generally be superfluous. The choice of ratios will vary with the circumstances and the objectives of the practitioner.

We have also found that surfactants have the effect of decreasing the time for crosslinking. Generally, in the absence of a surfactant, our combination of materials will crosslink in about two minutes at room temperature; when a surfactant is used also, this time is significantly reduced, and in the presence of our preferred class of surfactants, it is reduced to the neighborhood of twenty seconds, as determined by viscosity tests. About 0.1% to about 10% (based on the gelling agent) of surfactant is frequently advantageous also.

The phosphate derivatives we use are described in the literature as orthophosphate esters. They are similar to those used by Burnham in U.S. Pat. No. 4,200,540 and 4,316,810. Griffin U.S. Pat. Nos. 4,174,283 and 4,153,649, and Harris et al in U.S. Pat. No. 4,622,155, having the structural formula

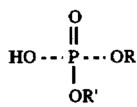

where R is a straight or branched chain alkyl, aryl, alkoxy, or alkaryl group having about 6 to about 18 carbon atoms and R' is hydrogen or an aryl, alkaryl, alkoxy, or alkyl group having up to about 18 carbon atoms. This structural formula will be referred to elsewhere herein as $HPO_4RR'$.

In the fracturing fluid, the iron from the ferric sulfate or other ferric salt such as ferric ammonium citrate, ferric butyl amine citrate, or ferric isopropylamine citrate, forms linkages with the available oxygen, generally in more than one phosphate group, thus forming small chains which cause the hydrocarbon to gel.

It has been demonstrated in the laboratory that our invention may be used to form hydrocarbon gels, and that the gels can be broken in a manner familiar to persons who work with hydrocarbon gels in the field such as by the addition of common alkaline materials. In the following examples, the procedure was to employ a laboratory Waring blender with a voltage regulator set at 30. 300 ml of Diesel oil was placed in the blender and the power turned on. The phosphate ester preparation was first added and after it was blended, the ferric salt solution was introduced by pipette. The time was recorded from the initial introduction of the ferric compound to the gel point, determined by a concave shape of the material in the blender.

Blending was continued to determine the time required to reach maximum gel, which was estimated to be the first sign of conversion of the shape of the material to convex instead of concave. The blending was then stopped and the material transferred to a sample container, observing the consistency of the gel. Brookfield viscosity readings were then taken as shown in the Table I.

In the examples below, Composition M is about two-thirds phosphate ester of the above formula $HPO_4RR'$, together with triethanolamine, and solvent. Composition L contains about two-thirds phosphate ester $HPO_4RR'$, together with triethylamine, and high flash aliphatic solvent. Composition K is two-thirds of the same phosphate ester and 15.5 g 45% KOH, also with a solvent. Composition F contains about 27% ferric sulfate, together with ethylene glycol, mixed surfactants, triethanolamine, and water. In each case, the amounts of composition M shown were added first to the Diesel oil and blended; then the amount shown of Composition F was added and blended. Results are presented in Table I.

TABLE I

| Ex | M | F | X-link | Invers | Spindle | 5 min | 30 min | 60 min |
|---|---|---|---|---|---|---|---|---|
| 1 | 3 ml | 3 ml | 20 sec | 30 sec | #3 | 2500 | — | 3890 |
| 2 | 3 ml | 3 ml | 20 sec | 30 sec | #3 | 2300 | — | 3460 |
| 3 | 3 ml | 3 ml | 25 sec | 35 sec | #3 | 2375 | — | 3400 |
| 4 | 3 ml | 3 ml | 30 sec | 60 sec | #4 | 6360 | 11000 | 13800 |
| 5 | 3 ml | 3 ml | 30 sec | 55 sec | #4 | 7320 | 12300 | 13500 |
| 6 | 3 ml | 3 ml | 45 sec | none at 180 sec | | | | |
| 7 | 2 ml | 2 ml | 60 sec | 150 sec | #4 | — | — | — |
| 8 | 3 ml* | 3 ml | 20 sec | 55 sec | #3 | 10000& | — | 13000& |
| 9 | 6 ml* | 3 ml | 15 sec | 30 sec | #4 | — | — | 21500& |
| 10 | 2 ml° | 3 ml | 20 sec | 35 sec | #4 | 13650& | — | 13850& |

*Composition L used instead of M
°Composition K used instead of M
&rotation at 10 rpm Persons skilled in the art will recognize from Table I that the formulations make excellent gels.

In a separate experiment, it was shown that the order of addition of the phosphate ester solution (sometimes herein called the gellant) and the ferric sulfate (or other iron salt such as ferric ammonium citrate) component (activator) is not important. In this experiment, 6.16 g deionized water and 1.3 g ferric sulfate were added to 85.95 g Diesel oil and mixed with the blender; then 0.4 ml of phosphate esters of the formula $HPO_4RR'$ was added and inversion took place in about one minute.

The data in Table II demonstrate that our hydrocarbon gel former will operate in the presence of significant amounts of water; indeed the viscosity increases with increasing amounts of water. In this experiment, an initial mixture was made as in the paragraph immediately above with 4 g of gellant and 10 g of activator in about 250 g of Diesel oil. Water was then added incrementally and the viscosity measured immediately.

TABLE II

| Cumulative Water, % | Viscosity (511 sec$^{-1}$) |
|---|---|
| 0.65% | 1 cp |
| 1.27% | 6 cp |
| 2.16% | 12 cp |
| 2.78% | 19 cp |
| 3.50% | 26 cp |
| 4.18% | 29 cp |
| 5.06% | 30 cp |
| 6.17% | * |
| 7.58% | * |
| 8.38% | * |
| 10.41% | * |
| 14.78% | * |
| 20.2% | * |

*Dial bouncing and unreadable; excellent lipping gel observed.

Additional tests were made as shown in Table III, which records the viscosities achieved by various combinations within our invention.

TABLE III

| ml M | ml F | cps | ml other |
|---|---|---|---|
| 3 | 3 | 13,800 | |
| 3 | 3 | 13,500 | |
| 2 | 2 | (bouncing dial) | |
| a | 3 | 13,000 | |
| b | 3 | 21,500 | 6TEA* |
| c | 3 | 13,900 | 2KOH |
| 3 | 3 | 15,000 | |
| 3 | 3 | 16,000 | |
| d | 3 | 5,800 | low acid value PE |
| e | 3 | 9,400 | high acid value PE |
| f | 3 | 20,800 | KOH |
| g | 3 | 11,300 | ½KOH |
| 3 | 3 | 7,000 | ¼KOH |
| 3 | 3 | 8,600 | no TEA in F |
| 3 | 3 | 8,700 | KOH in M; no TEA in F |
| 3 | 3 | 14,500 | KOH in M; no TEA |
| 3 | 3 | 13,400 | |
| 3 | 3 | — | 4400 cps @ 20 rpm |
| i | 3 | 9,300 | |
| j | 3 | 20,400 | |
| 2 ml | 3 | 12,700 | |
| 2 ml | 1.5 | 8,300 | |
| k | 1.5 | 10,000 | |
| l | 1.5 | 12,500 | 2 ph est; KOH; 1.5 Fe |
| 3 | 3 | 14,700 | |
| m | 3 | 20,000 | |
| 3 | 3 | 23,000 | 0.25 g $Na_2CO_3$ |
| n | 3 | 21,000 | |
| o | 3 | 18,400 | 0.25 g $Na_2CO_3$ |
| 3 | 3 | 19,500 | 0.5 g $CaCl_2$ |
| p | 3 | 13,800 | 0.5 g $CaCl_2$ |
| 2 | 3 | 7,000 | |
| q | 3 | 11,600 | |
| r | 3 | 12,100 | |
| 3 | 3 | 10,500 | |
| 3 | 3 | 10,500 | Fe Citrate |
| 3 | 3 | 9,700 | |
| 3 | 3 | 6,800 | Fe Citrate |
| u | 3 | 8,200 | |
| v | 3 | 18,400 | $Na_2CO_3$ |
| w | 3 | 21,000 | $Na_2CO_3$ |
| x | 3 | 10,000 | |
| y | 3 | 11,000 | |

TABLE III-continued

| ml M | ml F | cps | ml other |
|---|---|---|---|
| aa | 2 | 6,700 | |
| bb | 1 | 780 | |
| cc | 4 | 12,300 | |
| dd | 3 | 13,000 | |
| ee | 4 | 12,200 | |
| ff | 5 | 12,000 | |
| gg | 6 | 11,500 | |
| hh | 7 | 12,300 | |
| ii | 9 | 11,500 | |
| jj | 11 | 11,400 | |
| kk | 13 | 13,300 | |
| ll | 17 | 11,800 | |
| mm | 3 | 10,900 | |
| nn | 3 | 14,700 | |
| oo | 2 | 14,900 | |
| pp | 4 | 14,900 | |
| qq | 6 | 12,500 | |
| rr | 8 | 12,700 | |
| ss | 11 | 10,400 | |
| tt | 15 | 7,600 | |

In Table III, the following notes apply to the column headed "ml Other":

| | |
|---|---|
| a | triethylamine with phosphate ester of M -- 3 ml |
| b | triethylamine with phosphate ester of M -- 6 ml |
| c | KOH with phosphate ester of M -- 2 ml |
| d | triethanolamine with varied phosphate ester -- 3 ml |
| e | triethanolamine with varied phosphate ester -- 3 ml |
| f | KOH with phosphate ester of M -- 3 ml |
| g | same as-f-with half as much KOH -- 3 ml |
| h | same as-g-with half as much KOH -- 3 ml |
| i,m,n,o,p | KOH with phosphate ester of M -- 3 ml |
| k,l | KOH with phosphate ester of M -- 2 ml |
| q,r,s | KOH with varied phosphate ester -- 2 ml |
| t,u,v,w,x,y | no alkali; phosphate ester of M -- 3 ml |
| aa | 3 ml non-neut phosphate ester; 2 ml F |
| bb | 3 ml non-neut phosphate ester; 1 ml F |
| cc | 3 ml non-neut phosphate ester; 4 ml F |
| dd | 3 ml KOH-treated phosphate ester; 3 ml F |
| ee | 3 ml KOH-treated phosphate ester; 4 ml F |
| ff | 3 ml KOH-treated phosphate ester; 5 ml F |
| gg | 3 ml KOH-treated phosphate ester; 6 ml F |
| hh | 3 ml KOH-treated phosphate ester; 7 ml F |
| ii | 3 ml KOH-treated phosphate ester; 9 ml F |
| jj | 3 ml KOH-treated phosphate ester; 11 ml F |
| kk | 3 ml KOH-treated phosphate ester; 13 ml F |
| ll | 3 ml KOH-treated phosphate ester; 17 ml F |
| mm | 3 ml non-neut phosphate ester; 3 ml F |
| nn | 3 ml non-neut phosphate ester; 2 ml F |
| oo | 3 ml M; 4 ml F |
| pp | 3 ml M; 6 ml F |
| qq | 3 ml M; 8 ml F |
| rr | 3 ml M; 11 ml F |
| ss | 3 ml M; 15 ml F |

From the above table III, it is apparent that a broad range of ferric salts, neutralizing agents, and other additives such as breakers, and other materials are not detrimental to the gelling abilities of our invention.

In the following Table IV, ferric salts as shown were used in combination with a standard 3 ml concentration of phosphate ester solution, some with KOH and some without, in 300 ml oil. The viscosity was measured with a #4 spindle at 10 rpm unless otherwise noted.

TABLE IV

| Iron salt | ml Fe | Viscosity | Comment |
|---|---|---|---|
| Fe Citrate | 3 | 6,800 | |
| Fe Citrate | 1 | 8,800 | |
| Fe Citrate | 3 | 16,700 | |
| Fe Citrate | 3 | 7,000+ | |
| Fe Citrate | 2 | 8,000 | |
| Fe Citrate | 2.5 | 3,300 | #3 spndl; 10 rpm |

TABLE IV-continued

| Iron salt | ml Fe | Viscosity | Comment |
|---|---|---|---|
| Fe Citrate | 2.5 | 3,200 | " |
| Fe Citrate | 2.5 | 3,200 | " |
| Fe Citrate | 2.5 | 2,700 | " |
| Fe Amm Sulf | 1 | 13,000 | |
| Fe Amm Sulf | 1 | 3,500 | (20 rpm) |
| Fe Amm Sulf | 1.5 | 14,700 | |
| Fe Amm Sulf | 1.5 | 15,000 | |
| Fe Chloride | 3 | 6,200 | |
| Fe Chloride | 2 | 7,600 | |
| Fe Sulfate | 1 | 9,700 | |
| Fe Sulfate | 1.5 | 14,000 | |
| Fe Sulfate | 1 | 7,000 | |
| Fe Amm Citrate | 3 | 12,000 | |
| Fe Gluconate | 3 | 4,600 | |

A further series of tests was conducted specifically with ferric ammonium citrate, ferric butylamine citrate, and ferric isopropylamine citrate. Ferric ammonium citrate was made according to the procedures described by Kruse and Mounce in U.S. Pat. No. 2,644,828, which is hereby incorporated herein by reference in its entirety. Because the structural formula of this composition is uncertain, i.e. the amount of $NH_3$ appears to vary with the color and physical form (see the listing of Ammonium Ferric Citrate in the Merck Index, Eighth Edition), we intend to include within the definition of ferric ammonium citrate any of the compositions contemplated within the aforesaid Kruse et al '828 patent. Both brown and green crystalline forms are described in the '828 patent. Generally, the procedure we followed was to form a solution of ammonium hydroxide and ferric sulfate, thus forming a ferric hydroxide precipitate, to which was added citric acid to form the ferric ammonium citrate. We intend to include ferric ammonium citrate made by any method, however. Likewise, the related, or derivative, as sometimes called herein, materials ferric butylamine citrate and ferric isopropylamine citrate are made in a similar manner, substituting butyl amine for the ammonium hydroxide or substituting isopropylamine for the ammonium hydroxide. In the case of isopropylamine, the designation "Fe IPA" in Table V means monoisopropylamine citrate and "Fe MIPA" means that the isopropylamine used to form the citrate was a mixture of monoisopropylamine, diisopropylamine, and triisopropylamine. Thus the term "ferric ammonium citrate or a lower alkyl substituted derivative thereof" is intended to include all versions of ferric ammonium citrate as described in the aforementioned Kruse and Mounce patent and those in which the ammonium moiety is substituted by amines having one, two or three alkyl groups, each having up to six carbon atoms. In each of the runs for which the results are shown in Table V, 3 ml of a 67% solution of the designated phosphate ester gelling agent (Phosphate esters R, S, and T in Table V are similar to those used in Table I, all within the previously defined formula $HPO_4RR'$) was mixed with a 3 ml solution (100% active) of the ferric citrate shown in 300 ml of Diesel oil and gels were formed by stirring at low speed for two minutes. As is known in the art, the Marsh funnel test (last column) measures the time for 100 ml of the gel to discharge from a standard funnel.

TABLE V

| Phosphate Ester | Citrate | Gel Eval | Formed (seconds) | Marsh (seconds) |
|---|---|---|---|---|
| R | Fe Amm | good | 12 | 235 |
| S | Fe Amm | excel | 17 | 291 |
| T | Fe Amm | excel | — | 239 |
| R | Fe Bu Am | excel | 13 | 94 |
| T | Fe Bu Am | excel | — | 17 |
| S | Fe Bu Am | excel | — | 7 |
| R | Fe IPA | excel | 27 | 18 |
| T | Fe IPA | excel | 31 | 10 |
| S | Fe IPA | excel | 24 | 6 |
| R | Fe MIPA | excel | 16 | 78 |
| S | Fe MIPA | excel | 44 | 6 |
| T | Fe MIPA | excel | — | 8 |

A further comparison of a phosphate ester gelled with ferric sulfate and the same phosphate ester gelled with ferric ammonium citrate showed the ferric ammonium citrate with a Fann 50 viscosity of 895–860 cps at 180° F. while the ferric sulfate had a Fann 50 viscosity of 400–300 cps at 180° F.

We claim:

1. Ferric alkylamine citrate wherein the alkyl amine is a mono- di- or triamine wherein each alkyl group has from one to six carbon atoms.

2. Ferric alkylamine citrate of claim 1 wherein the alkylamine is monobutlyamine.

3. Ferric alkylamine citrate of claim 1 wherein the alkylamine is monoisopropylamine.

4. Ferric alkylamine citrate of claim 1 wherein the alkylamine is triisopropylamine.

5. Method of making a ferric alkylamine citrate comprising forming a solution of ferric sulfate and an amine of the formula $R_2NR'$ wherein R' is an alkyl group having from one to six carbon atoms and each R is independently selected from hydrogen and alkyl groups having from one to six carbon atoms, adding citric acid thereto, and recovering a ferric alkylamine citrate.

6. Method of claim 5 wherein the alkylamine is monobutylamine.

7. Method of claim 5 wherein the alkylamine is monoisopropylamine.

8. Method of claim 5 wherein the alkylamine is triisopropylamine.

* * * * *